United States Patent
Ochiai et al.

(10) Patent No.: US 10,507,142 B2
(45) Date of Patent: Dec. 17, 2019

(54) FIBER ASSEMBLY AND LIQUID ABSORBENT SHEET-LIKE ARTICLE INCLUDING THE SAME AND METHOD OF MANUFACTURING FIBER ASSEMBLY

(71) Applicant: KURARAY KURAFLEX CO., LTD., Okayama-shi (JP)

(72) Inventors: Tooru Ochiai, Okayama (JP); Yasurou Araida, Osaka (JP); Sumito Kiyooka, Okayama (JP)

(73) Assignee: KURARAY KURAFLEX CO., LTD., Okayama-shi (JP)

( * ) Notice: Subject to any disclaimer, the term of this patent is extended or adjusted under 35 U.S.C. 154(b) by 43 days.

(21) Appl. No.: 15/540,084

(22) PCT Filed: Dec. 29, 2015

(86) PCT No.: PCT/JP2015/086579
§ 371 (c)(1),
(2) Date: Jun. 27, 2017

(87) PCT Pub. No.: WO2016/108285
PCT Pub. Date: Jul. 7, 2016

(65) Prior Publication Data
US 2018/0263825 A1  Sep. 20, 2018

(30) Foreign Application Priority Data
Dec. 29, 2014  (JP) .................. 2014-267062

(51) Int. Cl.
| | |
|---|---|
| A61F 13/49 | (2006.01) |
| A61F 13/15 | (2006.01) |
| A61F 13/511 | (2006.01) |
| D04H 1/425 | (2012.01) |
| D04H 1/492 | (2012.01) |
| A61F 13/53 | (2006.01) |

(52) U.S. Cl.
CPC ........ *A61F 13/15203* (2013.01); *A61F 13/15* (2013.01); *A61F 13/49* (2013.01); *A61F 13/511* (2013.01); *A61F 13/53* (2013.01); *D04H 1/425* (2013.01); *D04H 1/492* (2013.01); *A61F 2013/15422* (2013.01); *A61F 2013/15447* (2013.01); *A61F 2013/15463* (2013.01); *A61F 2013/530182* (2013.01); *A61F 2013/530343* (2013.01); *D10B 2201/00* (2013.01); *D10B 2401/02* (2013.01); *D10B 2401/06* (2013.01); *D10B 2509/026* (2013.01)

(58) Field of Classification Search
USPC ........................................ 162/157.1
See application file for complete search history.

(56) References Cited

U.S. PATENT DOCUMENTS

| | | | |
|---|---|---|---|
| 3,485,705 A | 12/1969 | Harmon | |
| 9,873,964 B2 * | 1/2018 | Collins | ............... A61K 8/0208 |
| 2001/0000585 A1 | 5/2001 | Cruise et al. | |
| 2012/0125547 A1 | 5/2012 | Akai | |
| 2013/0115837 A1 | 5/2013 | Kitchen et al. | |
| 2014/0259579 A1 | 9/2014 | Cheng et al. | |
| 2014/0318726 A1 | 10/2014 | Collins et al. | |
| 2014/0318729 A1 | 10/2014 | Collins et al. | |
| 2017/0073863 A1 | 3/2017 | Collins et al. | |

FOREIGN PATENT DOCUMENTS

| | | | |
|---|---|---|---|
| CN | 104024509 A | 9/2014 | |
| EP | 2776616 | * 12/2018 | ............. D21H 13/08 |
| GB | 1209775 A | 10/1970 | |
| JP | 9-31817 A | 2/1997 | |
| JP | 10-315142 A | 12/1998 | |
| JP | 2001-521846 A | 11/2001 | |
| JP | 2002-61060 A | 2/2002 | |
| JP | 3621567 B2 | 2/2005 | |
| JP | 2006-291437 A | 10/2006 | |
| JP | 2006-326470 A | 12/2006 | |
| JP | 3871698 B2 | 1/2007 | |
| JP | 2008-111210 A | 5/2008 | |
| JP | 2009-132055 A | 6/2009 | |
| JP | 2010-81987 A | 4/2010 | |
| JP | 2010-207811 A | 9/2010 | |
| JP | 2010-222717 A | 10/2010 | |
| WO | 99/23291 A1 | 5/1999 | |
| WO | 2010/143722 A1 | 12/2010 | |

(Continued)

OTHER PUBLICATIONS

CN 104024509, Collins, et al., machine translation, Sep. 2014.*
International Search Report dated Mar. 15, 2016 in PCT/JP2015/086579 filed Dec. 29, 2015.
Extended European Search Report dated Oct. 26, 2018 in Patent Application No. 15875411.9, 7 pages.

(Continued)

*Primary Examiner* — Mark Halpern
(74) *Attorney, Agent, or Firm* — Oblon, McClelland, Maier & Neustadt, L.L.P.

(57) ABSTRACT

A fiber assembly including fibrils including a fibril which is a part of a fiber extending in a direction of thickness of the fiber assembly and including a network structure formed with a binding portion resulting at least any from binding between fibrils and binding between a fibril and a fiber in at least any end portion in the direction of thickness of the fiber assembly and a liquid absorbent sheet-like article including the same as well as a fiber assembly which is excellent in diffusion of a liquid particularly at a surface and absorption thereof in the inside and includes fibrils and a liquid absorbent sheet-like article including the same as well as a method of manufacturing the fiber assembly can be provided.

16 Claims, 8 Drawing Sheets

(56) References Cited

FOREIGN PATENT DOCUMENTS

| | | | |
|---|---|---|---|
| WO | WO 2013/067557 A1 | 5/2013 | |
| WO | WO 2013067557 * | 5/2013 | ............ D21H 13/08 |
| WO | WO 2014/151480 A1 | 9/2014 | |

OTHER PUBLICATIONS

Combined Chinese Office Action and Search Report dated Nov. 14, 2018, in Patent Application No. 201580071629.8 (with English translation), 13 pages.

* cited by examiner

FIG.2
(a)
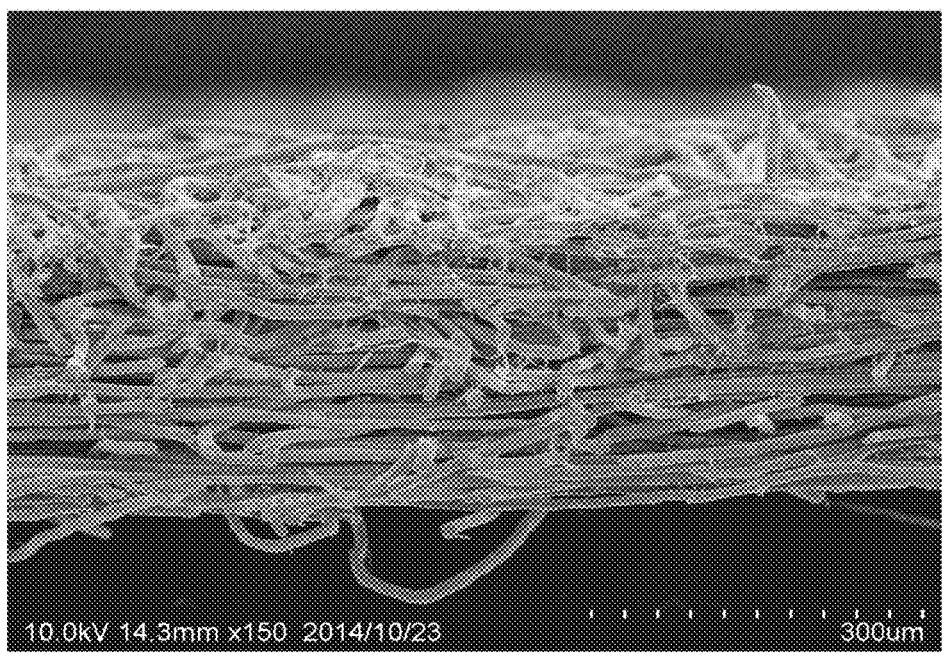
(b)
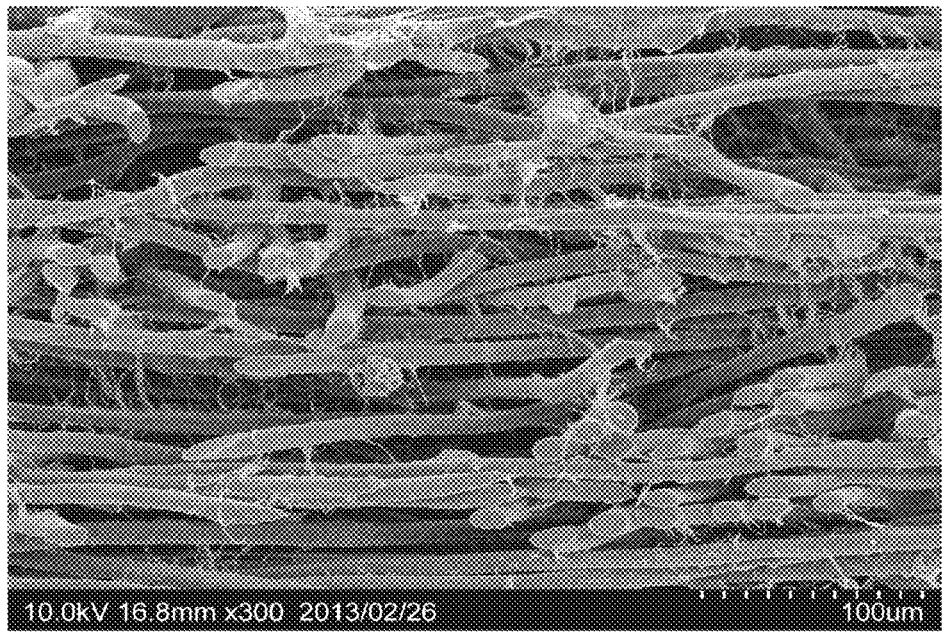

FIBER ASSEMBLY AND LIQUID ABSORBENT SHEET-LIKE ARTICLE INCLUDING THE SAME AND METHOD OF MANUFACTURING FIBER ASSEMBLY

CROSS-REFERENCE TO RELATED APPLICATIONS

This application is a National Stage of PCT/JP2015/086579, which was filed on Dec. 29, 2015. This application is based upon and claims the benefit of priority to Japanese Application No. 2014-267062, which was filed on Dec. 29, 2014.

TECHNICAL FIELD

The present invention relates to a fiber assembly low in density and excellent in diffusion of a liquid particularly at a surface and absorption thereof in the inside and a method of manufacturing the same. The present invention also relates to a liquid absorbent sheet-like article including such a fiber assembly according to the present invention.

BACKGROUND ART

For example, an absorbent article including a web having long crimped fibers oriented in one direction and having a highly-absorbent polymer embedded and carried therein has been known as a sheet excellent in diffusion of a liquid and absorption thereof in the inside (see Japanese Patent No. 3871698 (PTD 1)). In order to realize diffusibility and absorptiveness, however, the absorbent article disclosed in PTD 1 achieves the function with an extremely complicated structure based on combination of materials different in form such as calamus long in fiber, a highly-absorbent polymer, and tissue paper or based on requirement for a stack structure of materials and structures different from one another.

A waste ink absorber having a diffusion layer formed from fiber sheets which contain fibers having a standard moisture regain lower than 5% at least on one side of a liquid retaining layer which contains fibers having a standard moisture regain not lower than 5% and is formed from entangled fiber sheets has been known (see Japanese Patent No. 3621567 (PTD 2)). In order to maintain a form of the fiber sheet forming the diffusion layer, however, the waste ink absorber disclosed in PTD 2 achieves that function by employing a thermally fusible fiber component which is not directly relevant to a diffusion and absorption function or by employing a complicated layered structure for that function.

Japanese Patent Laying-Open No. 2010-222717 (PTD 3) discloses a method of manufacturing nanofibers by fibrillating fibers in a direction of length by applying cavitation energy to a fiber assembly and at least partially converting the fibers forming the fiber assembly into nanofibers. According to the background art in PTD 3, in connection with "fibrils", "A crack is produced in parallel to the direction of length of fibers by applying impact force in a direction of a diameter of fibers (except for glass fibers or metal fibers). A phenomenon that a crack is produced in a fiber and the fiber is split into finer fibers is called fibrillation, and the split fibers are called fibrils (fine fibers). The fibril is considered to be formed as an assembly of microfibrils which are finest fibers specific to each fiber material."

For example, Japanese Patent Laying-Open No. 2009-132055 (PTD 4) discloses as a technique using such fibrils, a friction material for a car which is derived from a single-layer fabric containing liquid crystal high-polymer fibers and has more fibrils in a surface layer portion on a side of a friction surface than in a surface layer portion on a side of the other surface.

CITATION LIST

Patent Document

PTD 1: Japanese Patent No. 3871698
PTD 2: Japanese Patent No. 3621567
PTD 3: Japanese Patent Laying-Open No. 2010-222717
PTD 4: Japanese Patent Laying-Open No. 2009-132055

SUMMARY OF INVENTION

Technical Problem

Though a technique focusing on fibrils has conventionally been existed, a fiber assembly excellent in strength in spite of being low in density and excellent in diffusion of a liquid particularly at a surface and absorption thereof in the inside by making use of fibrils and a liquid absorbent sheet-like article including the same have not yet been proposed.

The present invention was made to solve the problems above and an object thereof is to provide a fiber assembly excellent in diffusion of a liquid particularly at a surface and absorption thereof in the inside by making use of fibrils and a liquid absorbent sheet-like article including the same as well as a method of manufacturing the fiber assembly.

Solution to Problem

The present invention provides a fiber assembly including a fibril which is a part of a fiber extending in a direction of thickness of the fiber assembly and including a network structure formed with a binding portion resulting at least any from binding between fibrils and binding between a fibril and a fiber in at least any end portion in the direction of thickness of the fiber assembly.

The fiber assembly according to the present invention preferably includes a region where an average number of fibrils extending in the direction of thickness of the fiber assembly is not smaller than 10 when 100 sections of 300 µm wide×a thickness of the fiber assembly in a cross-section in a direction perpendicular to a direction of a length of fiber are observed.

The fiber assembly according to the present invention preferably has a void ratio not lower than 50%.

The fiber assembly according to the present invention preferably has a rupture strength not lower than 3 N/5 cm and a rupture elongation not higher than 300%. The fiber assembly further preferably has a rupture strength not lower than 10 N/5 cm in a machine direction and not lower than 3 N/5 cm in a cross direction and preferably has a rupture elongation not higher than 100% in the machine direction and not higher than 300% in the width direction.

The fiber assembly according to the present invention is preferably in a form of a sheet.

The fiber assembly according to the present invention is preferably formed from a trunk portion which keeps a shape like a sheet and a branch portion having the network structure, and a diameter of fibers forming the trunk portion and a diameter of fibers forming the branch portion is from 5000:1 to 5:1.

The fiber assembly according to the present invention preferably has a ratio of fibrillation within a range from 0.1 to 70%, the ratio of fibrillation being calculated from an expression $$\text{ratio of fibrillation (\%)} = (A-B)/A \times 100$$

where A represents an average value of a cross-sectional area of 100 fibers in a direction perpendicular to a direction of a length of fiber in a region formed with fibers without fibrils of the fiber assembly on an outer side and B represents an average value of a cross-sectional area of 100 fibers in a region including fibers with fibrils on an outer side formed in at least any end portion in the direction of thickness of the fiber assembly.

In the fiber assembly according to the present invention, fibers with fibrils are preferably cellulose fibers manufactured through solvent spinning.

In the fiber assembly according to the present invention, preferably, the network structure is formed by binding between a fibril and a fiber main body, binding between fibrils, and entangling between fibrils.

The fiber assembly according to the present invention is preferably a nonwoven fabric. In this case, the fiber assembly has a mass per unit area further preferably from 10 to 1000 g/m$^2$, a thickness further preferably from 0.05 to 10 mm, and an apparent density further preferably from 0.01 to 0.5 g/cm$^3$. The nonwoven fabric according to the present invention is particularly preferably a spunlace nonwoven fabric.

The present invention also provides a liquid absorbent sheet-like article including the fiber assembly according to the present invention described above.

The present invention further provides also a method of manufacturing a fiber assembly including forming a fiber assembly precursor by assembling a plurality of fibers and forming a network structure having a binding portion resulting at least any from binding between fibrils and binding between a fibril and a fiber by forming fibrils extending in a direction of thickness of the fiber assembly by applying cavitation energy from at least one side in a direction of thickness of the fiber assembly precursor.

Advantageous Effects of Invention

According to the present invention, a fiber assembly excellent in strength while being low in density and excellent in diffusion of a liquid particularly at a surface by making use of fibrils can be provided, which can efficiently transmit, when a liquid is applied to the fiber assembly, the liquid from an end portion in a direction of thickness of the fiber assembly to the inside and absorb the liquid in the inside, with fibrils extending in a direction of thickness of the fiber assembly and a network structure formed with a binding portion resulting at least any from binding between fibrils and binding between a fibril and a fiber in at least any end portion in the direction of thickness of the fiber assembly.

BRIEF DESCRIPTION OF DRAWINGS

FIG. 2 is (a) a scanning electron micrograph showing a cross-sectional structure of the entire fiber assembly 1 according to the present invention and (b) a scanning electron micrograph showing a part of FIG. 2 (a) as being enlarged.

DESCRIPTION OF EMBODIMENTS

<Fiber Assembly>

Figure 1:
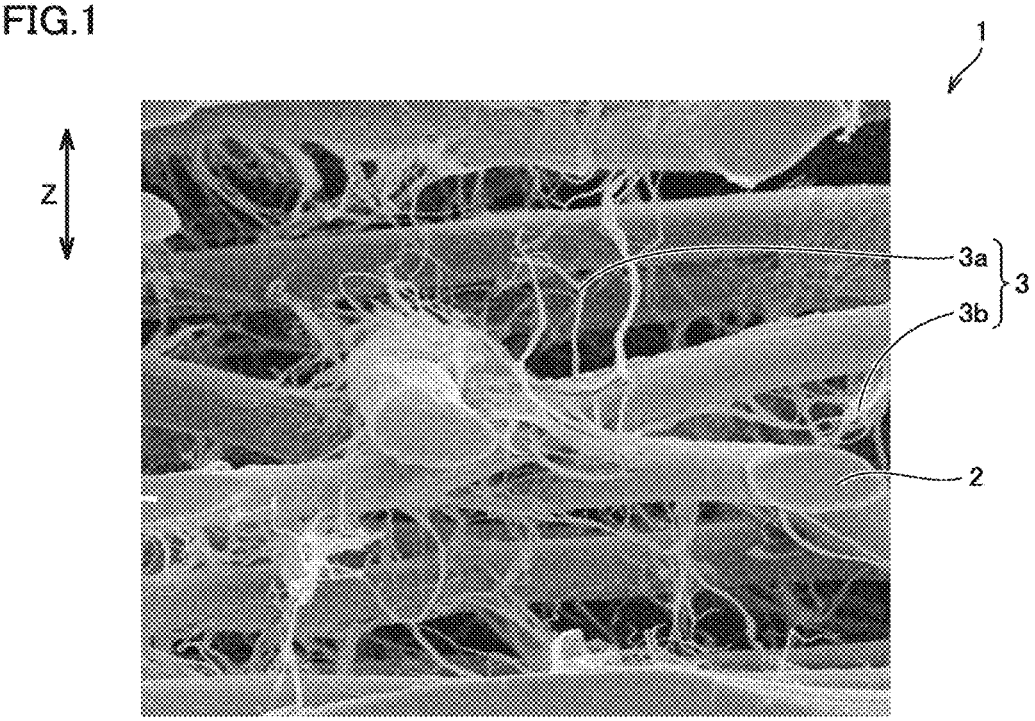
FIG. 1 is a scanning electron micrograph showing a cross-sectional structure of one preferred example of a network structure in a fiber assembly 1 according to the present invention.
Figure 3:
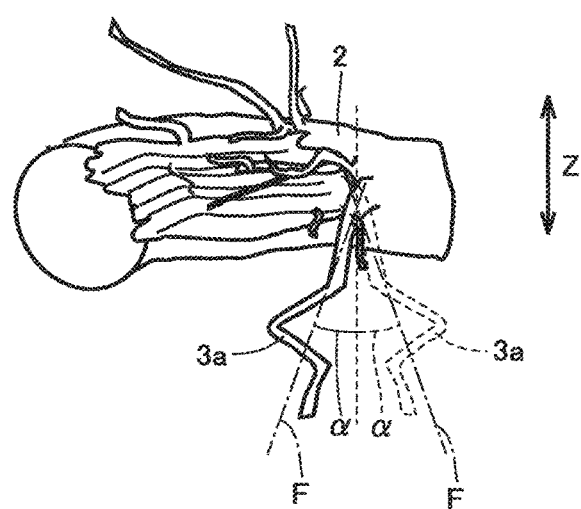
FIG. 3 is a schematic diagram for illustrating a fibril 3a extending in a direction of thickness of fiber assembly 1 according to the present invention.
Figure 4:
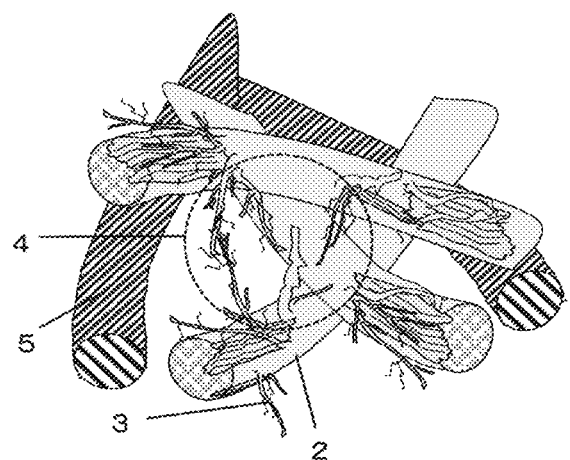
FIG. 4 is a diagram schematically showing a network structure 4 in fiber assembly 1 according to the present invention.

FIG. 1 is a scanning electron micrograph (1500×) showing a cross-sectional structure of one preferred example of a network structure in a fiber assembly 1 according to the present invention. FIG. 2 is (a) a scanning electron micrograph (150×) showing a cross-sectional structure of the entire fiber assembly 1 according to the present invention and (b) a scanning electron micrograph (300×) showing a part of FIG. 2 (a) as being enlarged. FIG. 3 is a schematic diagram for illustrating a fibril 3a extending in a direction of thickness of fiber assembly 1 according to the present invention and FIG. 4 is a diagram schematically showing a network structure 4 in fiber assembly 1 according to the present invention. Fiber assembly 1 according to the present invention is a fiber assembly which is an assembly of a plurality of fibers 2, includes fibrils 3 including a fibril 3a which is a part of fiber 2 extending in a direction of thickness Z of fiber assembly 1, and includes a network structure formed with a binding portion resulting at least any from binding between fibrils and binding between a fibril and a fiber in at least any end portion in the direction of thickness of the fiber assembly.

The "fiber assembly" in the present invention should only be an assembly of a plurality of fibers such as a weave (a textile), a knit, a lace, a felt, and a nonwoven fabric each of which is an assembly of a plurality of fibers, and a condition for manufacturing the same is not particularly restricted. A fiber assembly can be selected as appropriate depending on applications. For example, for applications in which a fiber assembly is repeatedly used, selection from a textile and a knit is preferred in terms of durability, and for single-use applications, a nonwoven fabric is preferably selected also in terms of cost. The fiber assembly according to the present invention also encompasses a fiber assembly in a form of a thin ribbon obtained by subsequent slitting of a structure and a fiber assembly processed into a card, a chip, or the like by punching or the like.

"Fibers" forming a fiber assembly include fibers at least partially containing fibrils, and it may be a mixture of fibers 2 containing fibrils 3 and fibers 5 not containing fibrils (fibers of a type the same as or different from a type of fibers containing fibrils), for example, as in an example shown in FIG. 4.

The "fibril" in the present invention refers to a finer fiber (a fine fiber) split (fibrillated) from fiber 2 as resulting from a crack produced in fiber 2, and encompasses both of what is called a "microfibril" having a diameter not smaller than 0.005 µm and smaller than 0.05 µm and what is called a "macrofibril" having a diameter not smaller than 0.05 µm and not greater than 5 µm. One of major features of the fiber assembly according to the present invention is that the fibrils include fibrils extending in direction of thickness Z of the fiber assembly. "Extending in direction of thickness Z of the fiber assembly" refers to such a condition that an angle a formed by a virtual straight line F which is a direction of extension of a fibril with respect to direction of thickness Z is within a range from −60° to +60° (FIG. 3 schematically shows an example in which angle a formed with respect to the direction of thickness has a positive numeric value (a solid line) and an example in which angle α formed with respect to the direction of thickness has a negative numeric value (a dashed line)). In observation of a cross-section of the fiber assembly, if vertical positional relation between fibers layered on each other in the direction of thickness is clear and binding between fibrils between upper and lower fibers can be confirmed, such a structure is also encompassed as a fibril "extending in direction of thickness Z of the fiber assembly" as defined in the present invention even though an angle as above cannot be measured.

The fiber assembly according to the present invention is more advantageous, by having such fibrils 3*a* extending in the direction of thickness, than a fiber assembly without fibrils extending in the direction of thickness in that a liquid can readily diffuse in the direction of thickness of the fiber assembly along fibrils extending in the direction of thickness and the liquid can efficiently be absorbed in the fiber assembly.

Fiber assembly 1 containing fibrils 3*a* extending in direction of thickness Z can be confirmed, for example, by using a scanning electron microscope (suitably, a scanning electron microscope S-3400N (manufactured by Hitachi High-Technologies Corporation)) and observing 100 sections of 300 µm wide×a thickness of fiber assembly in a cross-section in a direction perpendicular to a direction of length of fiber (which is the same as a cross-section in a machine direction of the fiber assembly which will be described later). The fiber assembly according to the present invention includes a region where an average number of fibrils extending in the direction of thickness of the fiber assembly in such observation is preferably not smaller than 10 and more preferably not smaller than 20. When an average number of fibrils extending in the direction of thickness of the fiber assembly in that region is smaller than 10, few fibrils extend in the direction of thickness and hence a function to absorb a liquid in the direction of thickness which is aimed by the present invention does not tend to sufficiently be obtained. When a magnification of the scanning electron microscope is set, for example, to 5000× or higher, fibrils extending in the direction of thickness as being more finely branched can be observed and precisely fibrils of several ten nanometers may be observed. It is impossible, however, to precisely count the number of those fibrils. Therefore, the number of fibrils extending in the direction of thickness in the present invention is counted only in a portion where fibrils reliably bind to a fiber in an image picked up, for example, by a scanning electron microscope at a magnification of 1000× and hence the upper limit value for the number of fibrils is not defined. So long as vertical positional relation between fibers layered on each other in the direction of thickness is clear and binding between fibrils between upper and lower fibers can be confirmed, such a structure is counted as a fibril extending in the direction of thickness even though an angle described above cannot be measured.

Fiber assembly 1 according to the present invention includes network structure 4 formed with a binding portion resulting at least any from binding between fibrils 3 (including also fibrils 3*a* extending in the direction of thickness) described above and binding between fibril 3 (including also fibril 3*a* extending in the direction of thickness) and fiber 2 in at least any end portion in the direction of thickness. Such network structure 4 can also be confirmed by observing a cross-section in the direction perpendicular to the direction of length of fiber as described above.

Such a fiber assembly according to the present invention can provide a fiber assembly excellent in strength while being low in density and excellent in diffusion of a liquid particularly at a surface by making use of fibrils, which can efficiently transmit, when a liquid is applied to the fiber assembly, the liquid from an end portion in the direction of thickness of the fiber assembly to the inside and absorb the liquid in the inside, with fibrils extending in the direction of thickness of the fiber assembly and a network structure formed with a binding portion resulting at least any from binding between fibrils and binding between a fibril and a fiber. Such a fiber assembly according to the present invention is particularly suitable for such an application as a liquid absorbent sheet-like article as will be described later.

Fiber assembly 1 according to the present invention has a void ratio preferably not lower than 50%, more preferably not lower than 60%, and particularly preferably not lower than 70%. When the fiber assembly has a void ratio lower than 50%, voids are too small and liquid retention capability may not be sufficient. Fiber assembly 1 according to the present invention has a void ratio preferably not higher than 97% and more preferably not higher than 95%. When a void ratio of the fiber assembly exceeds 97%, a fiber density of the fiber assembly is low and it may become difficult to maintain a shape thereof (for example, a form of a sheet). A void ratio of the fiber assembly can be calculated from a mass per unit area and a thickness of the fiber assembly, an average specific gravity of fibers, and the like.

The fiber assembly according to the present invention exhibits excellent rigidity by adhesion and reinforcement by fibrils with the network structure formed with a binding portion resulting at least any from binding between fibrils and binding between a fibril and a fiber as described above. The fiber assembly according to the present invention has at least a rupture strength preferably not lower than 3 N/5 cm and a rupture elongation not higher than 300%. Further preferably, a rupture strength in a machine direction (MD) is not lower than 8 N/5 cm (more preferably not lower than 20 N/5 cm) and a rupture strength in a cross direction (CD) is not lower than 3 N/5 cm (more preferably not lower than 5 N/5 cm). Preferably, a rupture elongation in MD is not higher than 100% (more preferably not higher than 80%) and a rupture elongation in CD is not higher than 300% (more preferably not higher than 250%). Fiber assembly 1 according to the present invention is thus excellent in strength while it is low in density. The rupture strength and the rupture elongation described above refer to values measured in conformity with JIS L1913 "test methods for short-fiber nonwovens."

The fiber assembly according to the present invention has a water retention ratio preferably within a range from 200 to 2000%, more preferably within a range from 300 to 2000%, and particularly preferably within a range from 400 to 2000%, depending on a purpose of use. When the fiber assembly has a water retention ratio lower than 200%, basically, the water retention ratio may be insufficient when the fiber assembly is used for a liquid absorbent sheet-like article. The limit of water retention by the fiber assembly is considered as 2000%.

Diffusibility of the fiber assembly according to the present invention is not particularly restricted either. A greater value for (a diffusion length in the machine direction (MD) of the fiber assembly)×(a diffusion length in the cross direction (CD) of the fiber assembly) which will be described later is more advantageous, and the value is preferably not smaller than 400, more preferably not smaller than 600, and particularly preferably not smaller than 800. When the fiber assembly has diffusibility lower than 400, the fiber assembly is considered as not having fibril networks in number sufficient to function even though the fiber assembly has fibril networks.

Fiber assembly 1 according to the present invention is preferably in a form of a sheet. The fiber assembly in a form of a sheet is more advantageous, by having an area and a thickness, than an example in which the fiber assembly according to the present invention is in a form other than a sheet (calamus, a fiber bundle, twisted yarns, or the like) in that a liquid component can be retained and diffused.

Figure 5:
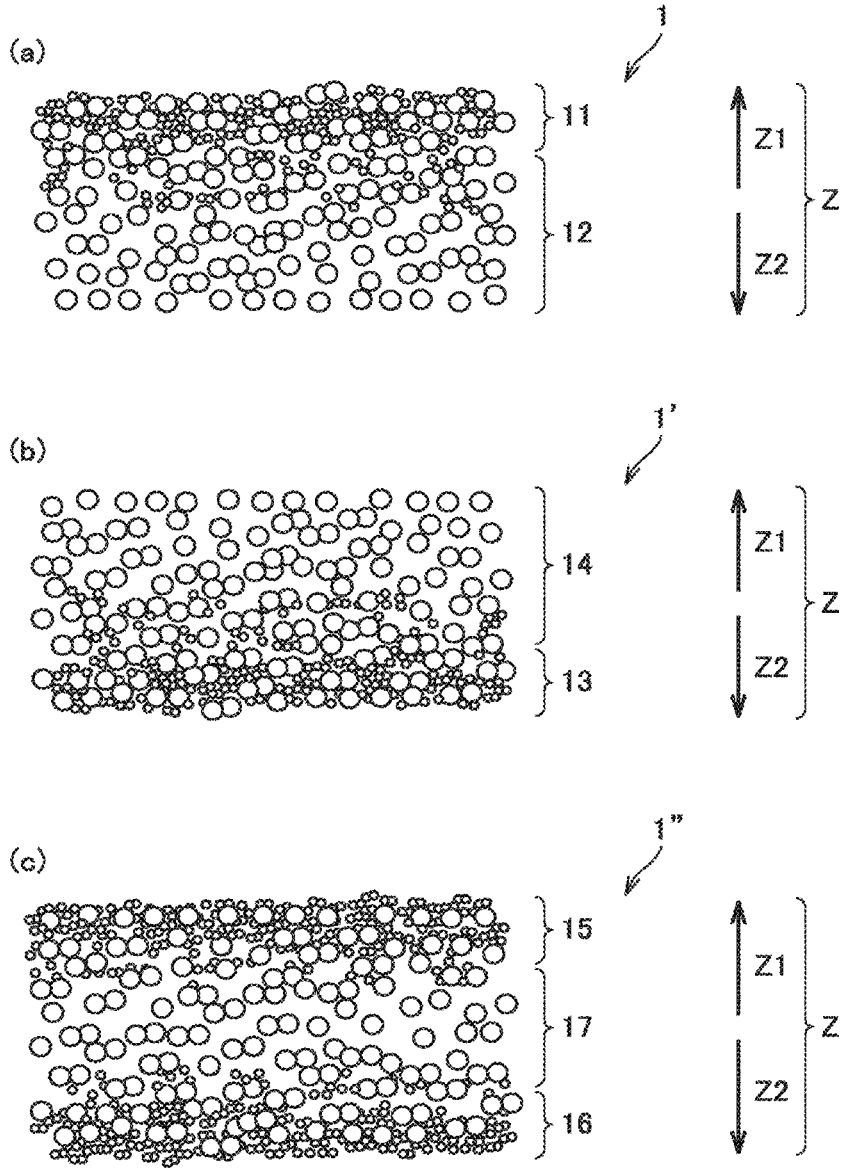
FIG. 5 is a diagram schematically showing various manners of the fiber assembly according to the present invention, with (a) showing fiber assembly 1 in a first example, (b) showing a fiber assembly 1' in a second example, and (c) showing a fiber assembly 1" in a third example.

FIG. 5 is a diagram schematically showing various manners of the fiber assembly according to the present invention, with (a) showing fiber assembly 1 in the example shown in FIGS. 1 and 2 (a first example), (b) showing a fiber assembly 1' in a second example, and (c) showing a fiber assembly 1" in a third example. The fiber assembly according to the present invention includes the network structure formed with a binding portion resulting at least any from binding between fibrils and binding between a fibril and a fiber in at least any end portion in the direction of thickness as described above. A portion having a network structure in the fiber assembly is referred to as a "branch portion" and a portion which does not have a network structure but keeps a form of a sheet is referred to as a "trunk portion." In fiber assembly 1 in the example shown in FIG. 5 (a), a branch portion 11 is formed only in an end portion on one side Z1 in the direction of thickness and other portions are defined as a trunk portion 12. In fiber assembly 1' in the example shown in FIG. 5 (b), a branch portion 13 is formed only in an end portion on the other side Z2 in the direction of thickness and other portions are defined as a trunk portion 14. In fiber assembly 1" in the example shown in FIG. 5 (c), branch portions 15 and 16 are formed in the end portion on one side Z1 in the direction of thickness and in the end portion on the other side Z2 in the direction of thickness, respectively, and other portions are defined as a trunk portion 17. Any of theses manners is encompassed as the fiber assembly of the invention of the present application. For example, in the manner shown in FIG. 5 (b), a surface to be used is not particularly limited. With one side in the direction of thickness of the fiber assembly being defined as a front surface side and the other side in the direction of thickness being defined as a rear surface side, the fiber assembly can suitably be applied to such an application that a liquid is hardly diffused over a front surface but the liquid is diffused over a rear surface with the network structure (such as an incontinence pad surface material, a surface material for a paper diaper, a surface material for a sanitary pad, and an agricultural water retention sheet).

Though network structure 4 may be formed over the entire surface in at least any end portion in the direction of thickness of the fiber assembly where the branch portion is formed, the network structure does not necessarily have to be formed over the entire surface. In this case, preferably at least 10% or more preferably at least 30% of the entire surface should only have the network structure.

Some of fibers forming the branch portion in the fiber assembly according to the present invention are fibrillated. Therefore, a portion other than the fibrillated portion (fibers forming the branch portion) is smaller in diameter than fibers forming the trunk portion not having the network structure. A diameter of the fiber forming the trunk portion described above and a diameter of the fiber forming the branch portion are preferably within a range from 5000:1 to 5:1 and more preferably within a range from 3000:1 to 10:1. When a diameter of a fiber forming the trunk portion is 5000 times as large as a diameter of a fiber forming the branch portion, many of fibrils tend to lose strength and to be cut, and formation of the network structure described above tends to be difficult. When a diameter of a fiber forming the trunk portion is less than five times as large as a diameter of a fiber forming the branch portion, strength of fibers to serve as a skeleton of a sheet form tends to be impaired.

Figure 6:
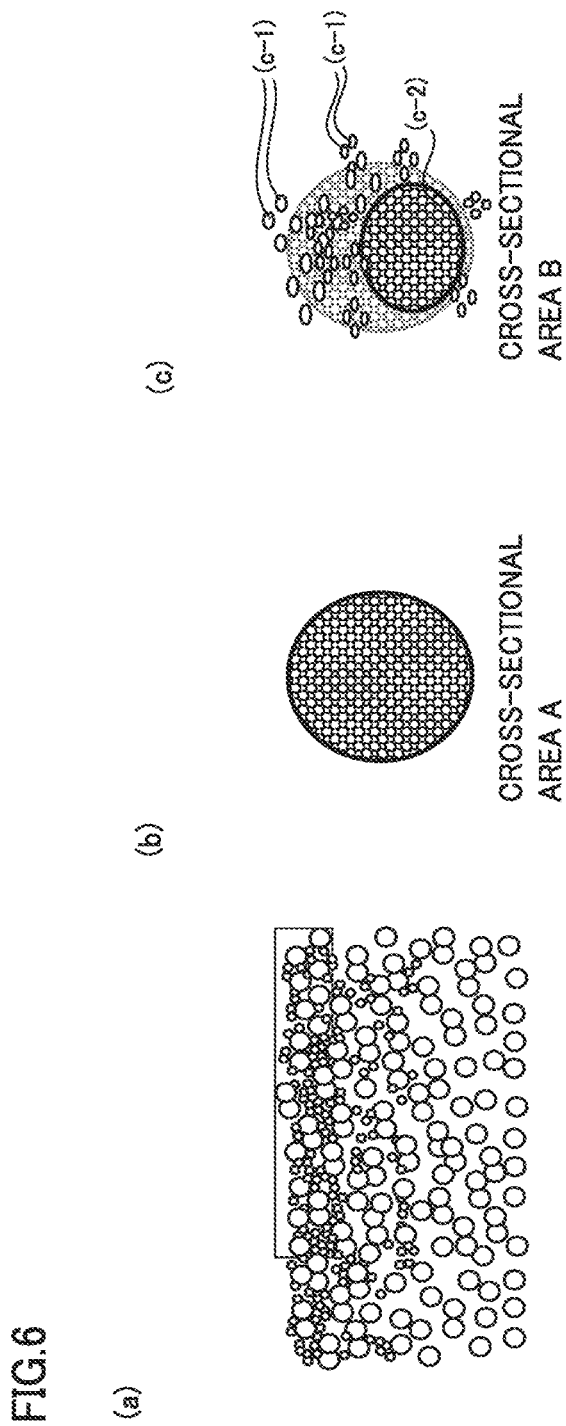
FIG. 6 is a schematic diagram for illustrating a ratio of fibrillation.

FIG. 6 is a schematic diagram for illustrating a ratio of fibrillation. FIG. 6 is (a) a schematic diagram of a cross-sectional structure of the fiber assembly according to the present invention, (b) a schematic diagram of a cross-section of fibers which form the fiber assembly according to the present invention and have a fibril structure in the inside, without any fibril appearing on an outer side, and (c) a schematic diagram of a cross-section of fibers which form the fiber assembly according to the present invention and have a fibril structure in the inside, with some fibrils appearing on the outer side. FIG. 6 shows (c-1) a cross-section of a fibril (branch portion) which appears on the outer side and (c-2) a cross-section of a fiber (trunk portion) which has been decreased in diameter as some fibrils come off from the outer side. A cross-sectional area A represents a cross-sectional area of a fiber at the time when the fiber without any fibril appearing is cut in a direction perpendicular to the direction of length (FIG. 6 (b)) and a cross-sectional area B represents a cross-sectional area of a fiber at the time when the fiber is cut in the direction perpendicular to the direction of length of the fiber decreased in diameter (trunk portion) (c-2). The fiber assembly according to the present invention has a ratio of fibrillation preferably within a range from 0.1 to 70%, the ratio of fibrillation being calculated from an expression ratio of fibrillation (%)=$(A-B)/A \times 100$ where A represents an average value of a cross-sectional area of 100 fibers in the direction perpendicular to the direction of length of fiber in a region formed with fibers without fibrils of the fiber assembly on the outer side and B represents an average value of a cross-sectional area of 100 fibers in a region including fibers having fibrils on the outer side formed in at least any end portion in the direction of thickness of the fiber assembly. As its name suggests, the ratio of fibrillation is expressed as a numeric value representing at which ratio fibers forming the network structure in the branch portion have been fibrillated. The fibers for which average value A is calculated are fibers which have a fibril structure in the inside but without any fibril appearing on the outer side, and fibers without a fibril structure in the inside are excluded from calculation. Fibers for which average value B is calculated are fibers which have a fibril structure in the inside, with some fibrils appearing on the outer side. When a ratio of fibrillation is lower than 0.1%, a network structure may not sufficiently be formed. When a ratio of fibrillation exceeds 70%, fibers to form a skeleton may be too thin and strength may become lower when the fibers are formed into a sheet. For such reasons that lowering in strength of the fiber assembly in a form of a sheet may lead to destruction of a structure due to tensile force in cutting of the fiber assembly in a form of a sheet into sheets, for example, in a subsequent process or slitting into ribbons, the ratio of fibrillation is more preferably within a range from 0.1 to 50% and particularly preferably within a range from 1.0 to 40%. The ratio of fibrillation can be controlled with a process condition in fibrillation as will be described later.

A ratio of fibrillation C on a side close to an end portion in the branch portion and a ratio of fibrillation D on a far side from the end portion (a side of the trunk portion) in the fiber assembly having the branch portion having the network structure only in the end portion on one side Z1 in the direction of thickness, for example, as shown in FIG. 5 (a), preferably satisfy relation of ratio of fibrillation C>ratio of fibrillation D. With such relation being satisfied, with such a distribution structure that in the branch portion having the network structure, a side closer to the end portion is higher in ratio of fibrillation (more network structures are present) and a liquid is readily diffused from that end portion in one fiber assembly and a side far from the end portion is lower in ratio of fibrillation (fewer network structures are present), the inside of the fiber assembly also serves as voids suited for retaining a liquid.

The fiber assembly according to the present invention may naturally be fibrillated also in a central portion in the direction of thickness, although not to such a high extent as in at least any end portion in the direction of thickness. When the central portion in the direction of thickness is thus fibrillated and only any end portion in the direction of thickness is high in ratio of fibrillation, the fiber assembly can suitably be applied to such an application as a filter, for example, by using a gradient of a fibril structure. When the central portion in the direction of thickness is fibrillated and opposing end portions in the direction of thickness are high in ratio of fibrillation, the fiber assembly can suitably be applied to such an application as a cleansing sheet which is, for example, less irritating to the skin and has high cleansing capability.

Examples of fibers 2 having fibrils 3 in the fiber assembly according to the present invention include non-thermoplastic fibers such as cellulose fibers, para-aramid fibers (polyparaphenylene terephthalamide fibers ("Kevlar®" manufactured by Du-Pont Toray Co. Ltd. and "Twaron" manufactured by Teijin Aramid B. V.); copoly(p-phenylene)-3,4-diphenyl ether terephthalamide fibers ("Technora®" manufactured by Teijin Techno Products Limited)), polyparaphenylene benzobisoxazole fibers ("Zylon" manufactured by Toyobo Co., Ltd.), cellulose-based fibers ("Tencel®" manufactured by Lenzing AG, "Cupro" manufactured by Asahi Kasei Corporation, and "NANOVAL" manufactured by NANOVAL GmbH & Co. KG), wholly aromatic polyester fibers ("Vectran" manufactured by Kuraray Co., Ltd.), polyketone fibers ("Cyberlon" manufactured by Asahi Kasei Corporation), ultrahigh molecular weight polyethylene fibers ("Dyneema®" manufactured by Toyobo Co., Ltd. and "Spectra" manufactured by Honeywell International Inc.), meta-aramid fibers (poly(metaphenylene isophthal amide) fibers (trademark "Nomex" manufactured by DuPont) and "Teijinconex" manufactured by Teijin Techno Products Limited), and polyvinyl alcohol based fibers ("Kuraron" manufactured by Kuraray Co., Ltd.), and these fibers are preferred because they are highly-oriented fibers. At least any selected from among polyketone (PK) fibers, polyether ketone (PEK) fibers, polyether ketone ketone (PEKK) fibers, and polyether ether ketone (PEEK) fibers in which at least 95 mass % of repeating units is composed of 1-oxotrimethylene represents an example of the polyketone fibers. The cellulose fibers are preferred because they are advantageous in their ability to suitably diffuse and absorb a liquid and in being general-purpose fibers and readily inexpensively available. Suitable examples of the cellulose fibers include natural cellulose fibers, regenerated cellulose fibers, and purified cellulose fibers. Specifically, natural cellulose fibers such as cotton, hemp, wool, and pulp, regenerated cellulose fibers such as rayon and cupro, and purified cellulose fibers such as Tencel® represent examples. Among these, Tencel® is preferred because it is high in strength owing to its high molecular weight and the molecular weight thereof hardly lowers even when it is wet. Though Tencel® is high in crystallinity and lower in hydrophilicity and extremely lower in liquid diffusion performance than the cellulose fibers such as rayon, in the present invention, the fiber assembly having improved diffusibility can be obtained by exposing fibrils in some of Tencel® fibers to increase a surface area of the fibers themselves and forming a network structure by causing a fibril connected to a main body of a Tencel® fiber to establish hydrogen bond with or be entangled with a main body of other Tencel® fibers or fibrils.

Though fineness (fineness of fibers 2 forming the trunk portion) of fibers 2 having fibrils 3 in a state before formation of fibrils is not particularly restricted, the fineness is preferably within a range from 0.01 to 5.5 dtex. When fineness of fibers 2 having fibrils 3 is lower than 0.01 dtex, strength of the fibers tends to be low and strength of the fiber assembly tends to be low. When fineness of fibers 2 having fibrils 3 exceeds 5.5 dtex, a distance between fibers in forming the fiber assembly into a sheet increases and formation of the network structure with the fibrils tends to be difficult. For such a reason that strength is achieved and a moderate fiber space (voids) can suitably be provided, fineness of fibers 2 having fibrils 3 is more preferably within a range from 0.1 to 3.3 dtex and particularly preferably within a range from 0.9 to 2.2 dtex. A plurality of fibers different in fineness (for example, a plurality of cellulose fibers different in fineness) in a state before formation of fibrils may naturally be employed as being mixed as fibers 2 having fibrils 3.

In connection with a fiber length of fibers 2 having fibrils 3 in a state before formation of fibrils, long fibers may be used in an example in which the fiber assembly according to the present invention is formed from a textile or a knit, or short fibers having a length, for example, in a range from 25 to 60 mm may naturally be used. When the fiber assembly according to the present invention is formed from a nonwoven fabric with a conventionally known appropriate method such as spun-bonding or melt blowing as well, long fibers or short fibers within a range from 32 to 51 mm in a dry-laid method may be employed. When short-cut fibers like a wet-laid type are used in a method of manufacturing a nonwoven fabric, a formed fiber assembly has a high density and such a fiber assembly is not preferred because voids among fibers necessary for forming a network with fibrils cannot be secured. A plurality of fibers different in fiber length (for example, a plurality of cellulose fibers different in fiber length) in a state before formation of fibrils may naturally be employed as being mixed as fibers 2 having fibrils 3.

Fibers 2 having fibrils 3 in the fiber assembly according to the present invention are preferably cellulose fibers manufactured through solvent spinning. Examples of the cellulose fibers manufactured through such solvent spinning include Tencel® described above, which is a fiber spun by dissolving wood pulp with (N-methylmorpholine-N-oxide) serving as a solvent at a ratio of NMMO/water/cellulose=80%/10%/10%.

The fiber assembly according to the present invention may contain in the branch portion, fibers other than fibers 2 having fibrils 3 (for example, fibers 5 in the example shown in FIG. 4) (hereinafter also referred to as "other fibers"). The trunk portion may naturally contain such other fibers. Such other fibers can freely be selected depending on a purpose and are not particularly restricted. Examples of such other fibers include regenerated fibers obtained by once dissolving synthetic fibers, natural fibers, natural plant fibers, or animal protein fibers followed by chemical treatment for generation as fibers. Examples of the natural fibers may include cotton, silk, hemp, and wool. For making fibers bulky, polyester fibers may be mixed as other fibers. Conventionally known appropriate composite fibers having a core-in-sheath structure may be employed as other fibers.

Though fineness of other fibers is not particularly restricted, fineness within a range from 0.1 to 5.5 dtex is preferred and a range from 0.5 to 3.3 dtex is more preferred. When other fibers have fineness lower than 0.1 dtex, density of the fiber assembly becomes high when the fiber assembly is formed into a sheet and voids among fibers necessary for forming a network structure with fibrils do not tend to be secured. When other fibers have fineness exceeding 5.5 dtex, a distance between fibers at the time when the fiber assembly is formed into a sheet increases and formation of the network structure with fibrils tends to be difficult. A fiber length of other fibers is not particularly restricted either. Similarly to fibers having fibrils described above, long fibers may be used or short fibers preferably from 25 to 60 mm may naturally be used.

When other fibers are mixed, a ratio of mixing is not particularly restricted. Mixing of other fibers is preferred because provision of voids in the fiber assembly according to the present invention is facilitated. When a ratio of mixing of other fibers is high, on the other hand, formation of a network structure with fibrils tends to be difficult. Therefore, fibers having fibrils occupy preferably at least 20% and more preferably at least 50% in weight ratio of the total of fibers having fibrils and other fibers. When fibers having fibrils are lower than 20%, it is difficult to form the network structure as described above.

In the fiber assembly according to the present invention, the network structure is preferably formed by binding between a fibril and a fiber main body, binding between fibrils, and entangling between fibrils. Binding between a fibril and a fiber and binding between fibrils are considered as hydrogen binding. Entangling refers to a state that fibrils are entangled with each other. Formation of a network structure with fibrils can be confirmed with a scanning electron microscope described above.

The fiber assembly according to the present invention is preferably a nonwoven fabric when it is in a form of a sheet. A fiber assembly in a form of a sheet made of a nonwoven fabric is more advantageous than a fiber assembly in a form of a sheet made of a material other than the nonwoven fabric in that voids are more readily provided between fibers and the fiber assembly can be manufactured more inexpensively than a textile, although depending on a purpose of use.

When a fiber assembly in a form of a sheet is formed from a nonwoven fabric, a mass per unit area is not particularly restricted, however, it is preferably within a range from 10 to 1000 g/m², more preferably within a range from 15 to 800 g/m², and particularly preferably within a range from 20 to 500 g/m². When a mass per unit area is smaller than 10 g/m², it is difficult to obtain strength of the fiber assembly in a form of a sheet and voids in the direction of thickness of the fiber assembly is less likely to be provided. When a mass per unit area exceeds 1000 g/m², the fiber assembly in a form of a sheet is too thick and a portion having the network structure (the branch portion) tends be obtained only in the vicinity of a front surface and/or a rear surface of the fiber assembly.

When a fiber assembly in a form of a sheet is formed from a nonwoven fabric, a thickness is not particularly restricted either, however, the thickness is preferably within a range from 0.05 to 10 mm, more preferably a range from 0.10 to 8 mm, and particularly preferably a range from 0.20 to 5 mm. When the thickness is smaller than 0.05 mm, the number of fibers does not tend to be sufficient in the direction of thickness of the fiber assembly for forming the network structure. When the thickness exceeds 10 mm, the fiber assembly in a form of a sheet is too thick and a portion having the network structure (the branch portion) tends be obtained only in the vicinity of a front surface and/or a rear surface of the fiber assembly.

The fiber assembly in a form of a sheet is preferably formed from a spunlace nonwoven fabric. By forming the fiber assembly in a form of a sheet with a spunlace nonwoven fabric, it is more advantageous than an example in which a nonwoven fabric is formed with a method other than spunlacing in that it is not necessary to use an adhesive component such as a thermoplastic resin for obtaining a form and a strength of fibers as a sheet and a ratio of mixing fibers having fibrils can freely be set.

<Liquid Absorbent Sheet-Like Article>

The present invention also provides a liquid absorbent sheet-like article including the fiber assembly in a form of a sheet according to the present invention described above. Though the liquid absorbent sheet-like article according to the present invention encompasses an ink absorber, an incontinence pad, a surface material for a sanitary pad, and a surface material for a paper diaper, limitation thereto is not intended. The liquid absorbent sheet-like article according to the present invention broadly encompasses articles used for a purpose of absorption of a liquid such as a face mask, an application sheet, a wet wiper, an antiperspirant sheet, a wet wipe, and a liquid filter or articles used with a liquid being absorbed therein or a composite member achieving a desired function by using high diffusibility of the fiber assembly according to the present invention.

<Method of Manufacturing Fiber Assembly>

The present invention further provides also a method of suitably manufacturing the fiber assembly according to the present invention described above. The method of manufacturing a fiber assembly according to the present invention includes forming a fiber assembly precursor by assembling a plurality of fibers and forming a network structure having a binding portion resulting at least any from binding between fibrils and binding between a fibril and a fiber by forming fibrils extending in a direction of thickness of the fiber assembly by applying cavitation energy from at least one side in a direction of thickness of the fiber assembly precursor. With such a method of manufacturing a fiber assembly according to the present invention, the fiber assembly according to the present invention described above can suitably be manufactured, however, the fiber assembly according to the present invention is not limited to a fiber assembly manufactured with the fiber assembly according to the present invention.

In the method of manufacturing a fiber assembly according to the present invention, initially, a fiber assembly precursor is formed. The fiber assembly precursor can be formed by using fibers described above as preferred as fibers having fibrils or mixing the fibers described above as preferred as other fibers in some cases and by using an existing processing technique (a method of manufacturing a textile, a knit, a lace, a felt, and a nonwoven fabric (any of a dry-laid type and a wet-laid type)) without particularly being restricted. The fiber assembly precursor is preferably a nonwoven fabric obtained by three-dimensionally entangling fibers through spunlacing (hydroentanglement) in a dry-laying method. Though the fiber assembly precursor may naturally be formed from a plurality of layers, in that case, a layer formed from fibers (for example, Tencel® fibers) which are to be fibers having fibrils should be exposed on a side where cavitation energy will be applied next.

Then, cavitation energy is applied to the obtained fiber assembly precursor at least from one side in the direction of the thickness. This step may be performed in such a state that the fiber assembly precursor has been formed in the step described above or may be performed by taking out the fiber assembly precursor which has once been wound after it was formed.

A method of applying cavitation energy includes a method of applying cavitation energy by applying ultrasonic waves to the fiber assembly while the fiber assembly is immersed in a liquid defined as a medium (water is generally employed). When ultrasonic energy is applied, a method of disposing a fiber assembly in a medium near a horn which converts electric energy generated from an ultrasonic oscillator into mechanical oscillation energy and exposing the fiber assembly to ultrasonic waves is available. A direction of oscillation of ultrasonic waves is preferably longitudinal oscillation in a direction perpendicular to the fiber assembly. A distance between the fiber assembly and the horn is smaller than approximately 1 mm and preferably the fiber assembly is disposed at a distance of ¼ wavelength from the horn. The fiber assembly should only be disposed as being in contact with the horn.

A conveyor with a mesh structure is preferably employed as a support for the fiber assembly when cavitation energy is applied. Oscillation of a tip end portion of the ultrasonic horn generates a flow of a liquid defined as a medium in a direction the same as the direction of oscillation. The flow of the liquid orients fibrils which appear at the surface and in the inside of the fiber assembly in the direction of thickness and serves to form a network in the direction of thickness. As the support has an open pore structure like the mesh structure, a network of fibrils is satisfactorily formed in the direction of thickness.

The support is not limited to the mesh structure so long as the support is structured not to prevent a flow of a liquid defined as a medium, and it may be in a form of a plate having an open pore structure or a conveyor like a roller.

Intensity of cavitation and a time period of exposure to a cavitation medium should be adjusted depending on a type of fibers in a fiber assembly or a degree of fibrillation. As intensity of cavitation is higher, a rate of generation of fibrils becomes higher and fibrils finer and higher in aspect ratio tend to generated. A frequency of oscillation of ultrasonic waves is normally set to 10 to 500 kHz, preferably to 10 to 100 kHz, and further preferably to 10 to 40 kHz.

A temperature of a medium is not particularly limited and it is set preferably to 10 to 100° C. A treatment time period is different depending on a type of fibers in a fiber assembly, a form of a fiber assembly, and fineness. A ratio of fibrillation of the fiber assembly according to the present invention can be controlled also under this condition. The treatment time period is set to 0.1 second to 60 minutes, preferably to one second to ten minutes, and further preferably to five seconds to two minutes. Similarly to the treatment time period, a ratio of fibrillation of the fiber assembly according to the present invention can be controlled by the number of times of treatment. Productivity of the fiber assembly according to the present invention and uniformity in a fibril structure can be enhanced by performing treatment in multiple stages. Though the number of times of treatment is not particularly limited, treatment is preferably performed two or more times.

Though the present invention will specifically be described with reference to Examples below, the present invention is not limited thereto.

[Mass per Unit Area $(g/m^2)$]

A weight (g) is measured with a balance by taking a specimen having a size of 1 m wide×1 m long after leaving a sample in a standard state for 24 hours at a temperature of 20° C. and a humidity of 65% in conformity with JIS L1906. The obtained weight (g) was rounded off to a closest whole number and the result is defined as a mass per unit area.

[Thickness (μm)]

A thickness was measured by cutting a sample in an MD direction perpendicularly to a surface with a razor ("Feather Razor S Single Blade" manufactured by FEATHER Safety Razor Co., Ltd.) and observing a cross-section of a specimen with a digital microscope [Digital Microscope VHX-900 manufactured by Keyence Corporation].

[Density $(g/cm^3)$]

A density was calculated by dividing the mass per unit area $(g/m^2)$ by the thickness.

[Void Ratio (%)]

A void ratio (%) was calculated in accordance with an expression $$\text{void ratio (\%)}=100-((E/F/G)\times100)$$

where E represents a mass per unit area $(g/m^2)$, F represents a thickness (μm), and G represents an average specific gravity of fibers $(g/cm^2)$.

[Rupture Strength and Rupture Elongation]

A rupture strength and a rupture elongation in the machine direction (MD) and the cross direction (CD) of a fiber assembly were measured in conformity with JIS L 1913 "test methods for short-fiber nonwovens."

[Ratio of Fibrillation]

Initially, a cross-sectional area of a fiber not having a fibril in the fiber assembly was found. The fiber was cut at an angle orthogonal to a direction of length of the fiber or a fiber in the fiber assembly including the fiber and a cross-section thereof was micrographed with a scanning electron microscope S-3400N (manufactured by Hitachi High-Technologies Corporation). A cross-sectional area of the fiber was found by using the "measurement tool" of personal computer software Adobe Photoshop CS6 Extended. This procedure was performed for 100 fibers and an average value was defined as a fiber cross-sectional area A.

Then, a cross-sectional area of a fiber having a fibril in the fiber assembly was found. A cross-section could be observed by cutting a fiber of which fibril was exposed at an angle orthogonal to a direction of flow of fibers, the cross-section was micrographed with an electron microscope, and a cross-sectional area was found with the "measurement tool" of personal computer software Adobe Photoshop CS6 Extended. This procedure was performed for 100 fibers having fibrils and an average value was defined as a fiber cross-sectional area B.

A ratio of fibrillation in a region intermediate in the direction of thickness between an end portion and another end portion of the fiber assembly was calculated from the obtained average values in accordance with an expression ratio of fibrillation (%)=(fiber cross-sectional area A−fiber cross-sectional area B)/fiber cross-sectional area A×100.

[The Number of Fibrils Extending in Direction of Thickness]

A fiber was cut at an angle orthogonal to the direction of length of fiber in the fiber assembly, and an average number of fibrils (such fibrils that an angle α formed by straight line F with respect to direction of thickness Z was within a range from −60° to +60° as shown in FIG. 3) extending in the direction of thickness of the fiber assembly at the time when 100 sections of 300 μm wide×a thickness of the fiber assembly were observed with a scanning electron microscope S-3400N (manufactured by Hitachi High-Technologies Corporation) was calculated. So long as vertical positional relation between fibers layered on each other in the direction of thickness was clear and binding between fibrils between upper and lower fibers could be confirmed, such a structure was counted as a fibril extending in the direction of thickness even though an angle described above could not be measured.

[Water Retention Ratio]

One end of a fiber assembly in a form of a sheet having a size of 5 cm×5 cm was clipped and the fiber assembly was immersed in water for thirty seconds. Thereafter, the fiber assembly was left for one minute with a sheet surface being perpendicular to the direction of gravity so that water dripped. Thereafter, a weight was measured and a water retention ratio was measured based on an expression water retention ratio=[(I−H)/H]×100

(where H represents a weight of a fiber assembly before immersion and I represents a weight of the fiber assembly after water dripped).

[Diffusibility]

The fiber assembly in a form of a sheet was cut into a size of 10 cm×10 cm and rested on a flat base. Then, colored water obtained by adding 1 g of PILOT ink RED (INK-350-R) manufactured by Pilot Corporation to 100 g of ion exchanged water was prepared. A droplet (0.05 g) of the colored water was dropped onto the center of the fiber assembly in a form of a sheet with a syringe 1 cm from above and a length of diffusion of the colored water at a surface after ten minutes was found as a diffusion length A mm in the machine direction (MD) of the fiber assembly or a diffusion length B mm in the cross direction (CD) perpendicular thereto. Diffusibility was determined based on a value calculated by multiplying a value for diffusion length A with a value for diffusion length B.

[Adhesiveness]

Figure 7:
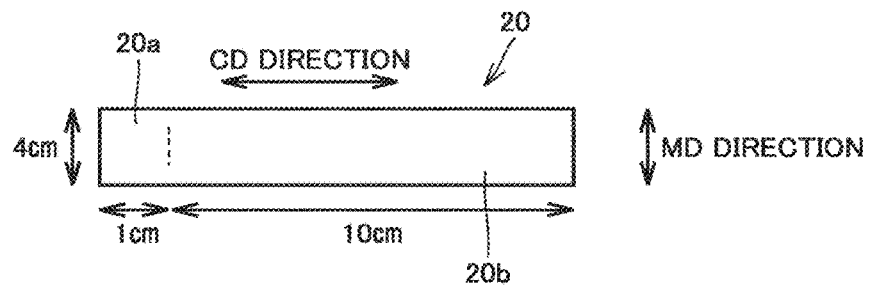
FIG. 7 is a schematic diagram for illustrating an adhesiveness test in an Example.
Figure 8:
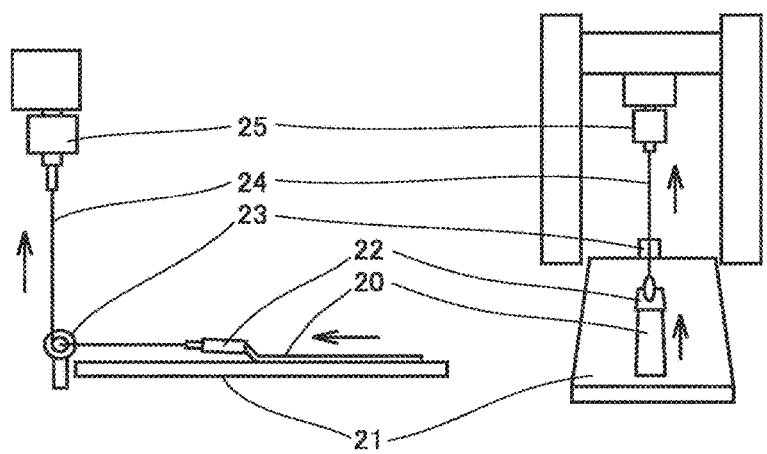
FIG. 8 is a schematic diagram for illustrating the adhesiveness test in the Example.
Figure 9:
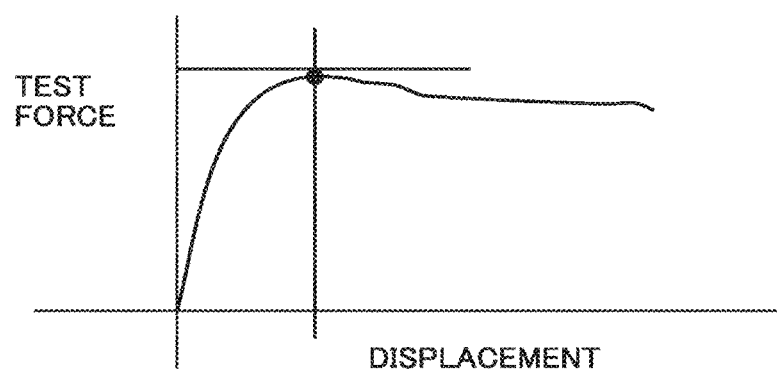
FIG. 9 is a schematic diagram for illustrating the adhesiveness test in the Example.

Friction force was measured under ASTM-D1894 with a universal/tensile testing machine ("Autograph AGS-D" manufactured by Shimadzu Corporation). As shown in FIG. 7, a sample 20 was cut into 4.0 cm in the MD direction×11.0 cm in the CD direction and a grip portion 20a was set to 1 cm long and a contact portion 20b was set to 10 cm long in the CD direction. This sample was impregnated with a cosmetic ("Freshel Essence Lotion AL" manufactured by Kanebo Cosmetics Inc.) by amounts of two types of mass % shown below, with an application as a face mask being assumed. As shown in FIG. 8, a test to pull the sample by holding grip portion 20a of this sample 20 with a clip 22 in a direction shown with an arrow was conducted. Specifically, as shown in FIG. 8, an acrylic plate was fixed onto a table 21 for measuring friction force, and the sample was placed on the center (with a surface of a fibrillated end portion facing down in the fiber assembly according to the present invention). A load of 10 g/cm² was applied for ten seconds onto an area (contact portion) of MD 4.0 cm×CD 10.0 cm with a testing machine including a load cell 25 and thereafter a polyamide thread 24 was pulled horizontally with a pulley 23 being interposed. A peak value of test force obtained by pulling the sample horizontally in the CD direction at a speed of 20 mm/min. (a peak value shown in FIG. 9) was defined and measured as adhesiveness. Adhesiveness was measured under such a condition that the sample was impregnated up to 500 mass % with respect to the mass of the sample, as simulating an environment in a latter half of use of the face mask where high adhesiveness was required, and a value thereof was obtained.

[Release Ratio]

The fiber assembly in a form of a sheet was cut into a size of 5 cm×5 cm and impregnated with 900 wt % (an initial impregnation weight) of a beauty essence ("Freshel Essence Lotion AL" manufactured by Kanebo Cosmetics Inc.) with respect to a weight of the sheet. Then, 20 sheets of filter paper cut into a size of 10 cm×10 cm (Qualitative Filter Paper No. 2 manufactured by ADVANTEC) were layered and the fiber assembly sheet impregnated with the beauty essence was rested on the center of the filter paper (with a surface of a fibrillated end portion facing the filter paper in the example of the fiber assembly according to the present invention). After five minutes, the fiber assembly was removed from the filter paper and weighed, so that a release ratio was found from variation in weight in accordance with an expression release ratio(%)=J/K×100

(where J represents a value calculated by dividing an initial beauty essence impregnation weight by a weight of the beauty essence retained in the sheet after five minutes and K represents the initial beauty essence impregnation weight).

[Surface Frictional Strength]

The fiber assembly in a form of a sheet was cut into a size of 3.0 cm in the cross direction (CD)×25.0 cm in the machine direction (MD) and attached to Rubbing Tester Type-II (Gakushin-Type RT-200) manufactured by Daiei Kagaku Seiki Mfg. Co., Ltd. (with a surface of a fibrillated end portion facing up as a friction surface in the example of the fiber assembly according to the present invention). A mass of a rubbing finger was set to 200 g, a white cotton cloth (Kanakin No. 3) was attached to a front surface, and a state of the front surface of the fiber assembly in a form of a sheet was visually observed after the rubbing finger performed reciprocating motion ten times over the front surface of the fiber assembly sheet.

EXAMPLE 1

A semi-random web was made with CAD by using Tencel® (manufactured by Lenzing AG) having fineness of 1.7 dtex and a fiber length of 38 mm. Then, a three-dimensional hydroentangling treatment was performed. The web was placed on a porous support member made of a metal and two stages of nozzles provided with injection holes each having a diameter of 0.10 mm at an interval of 0.6 mm in the width direction of the web were used to sequentially inject water jets at water pressures of 4 MPa and 5 MPa for entangling. The front and the rear of the web were reversed by a conveyor, the web was placed on a polyester plain-woven mesh (OP-76 manufactured by Nippon Filcon Co., Ltd.) support, and the two stages of the nozzles were used to sequentially inject water jets at water pressures of 5 MPa and 6 MPa for three-dimensional entangling. Thereafter, the web was subjected to contact drying at a temperature of 130° C. with a cylinder dryer. A series of these treatments was performed at a speed of 50 m/min. and a spunlace nonwoven fabric (a fiber assembly precursor) having a mass per unit area of 74.6 g/m$^2$ was obtained.

Then, one surface of the spunlace nonwoven fabric was fibrillated through a water-bath ultrasonic process with the use of an ultrasonic processor manufactured by Seidensha Electronics Co., Ltd. at power of 1200 W, a frequency of 20 kHz, the number of stages of five, a water temperature of 25° C., and a speed of 1 m/min. on a support formed with a nylon plain-woven mesh (a wire diameter of 160 μm #200) manufactured by Kansai Wire Netting Co., Ltd. Table 1 shows results of evaluation of the obtained fiber assembly.

EXAMPLE 2

A semi-random web was made with CAD by using Tencel® (manufactured by Lenzing AG) having fineness of 1.7 dtex and a fiber length of 38 mm. Then, a three-dimensional hydroentangling treatment was performed. The web was placed on a porous support member made of a metal and two stages of nozzles provided with injection holes each having a diameter of 0.10 mm at an interval of 0.6 mm in the width direction of the web were used to sequentially inject water jets at water pressures of 2 MPa and 3 MPa for entangling. The front and the rear of the web were reversed by a conveyor, the web was placed on a polyester plain-woven mesh (OP-76 manufactured by Nippon Filcon Co., Ltd.) support, and the two stages of the nozzles were used to sequentially inject water jets at water pressures of 2 MPa and 3 MPa for three-dimensional entangling. Thereafter, the web was subjected to contact drying at a temperature of 130° C. with a cylinder dryer. A series of these treatments was performed at a speed of 50 m/min. and a spunlace nonwoven fabric (a fiber assembly precursor) having a mass per unit area of 19.9 g/m$^2$ was obtained.

Then, one surface of the spunlace nonwoven fabric was fibrillated through a water-bath ultrasonic process with the use of an ultrasonic processor manufactured by Seidensha Electronics Co., Ltd. at power of 1200 W, a frequency of 20 kHz, the number of stages of three, a water temperature of 30° C., and a speed of 2 m/min. on a support formed with a nylon plain-woven mesh (a wire diameter of 160 μm #200) manufactured by Kansai Wire Netting Co., Ltd. Table 1 shows results of evaluation of the obtained fiber assembly.

EXAMPLE 3

A nonwoven fabric having a mass per unit area of 950 g/m$^2$ (a fiber assembly precursor) was obtained by mixing 90 weight % of Tencel® (manufactured by Lenzing AG) having fineness of 1.7 dtex and a fiber length of 38 mm and 10 weight % of polyester fibers (Tetoron® manufactured by Toray Industries, Inc.) formed of polyethylene terephthalate having fineness of 1.6 dtex and a fiber length of 51 mm, cross-webbing the mixed fibers with a CAD method, and entangling the fibers through needle punching at 1000 punches/cm$^2$ from a front surface side and at 1000 punches/cm$^2$ from a rear surface side.

Then, opposing surfaces of the needle-punched nonwoven fabric was fibrillated through a water-bath ultrasonic process with the use of an ultrasonic processor manufactured by Seidensha Electronics Co., Ltd. at power of 2000 W, a frequency of 20 kHz, the number of stages of five, a water temperature of 30° C., and a speed of 1 m/min. on a support formed with a nylon plain-woven mesh (a wire diameter of 160 μm #200) manufactured by Kansai Wire Netting Co., Ltd. Table 1 shows results of evaluation of the obtained fiber assembly.

EXAMPLE 4

A semi-random web was fabricated with CAD by mixing 50 weight % of Tencel® (manufactured by Lenzing AG) having fineness of 1.7 dtex and a fiber length of 38 mm and 50 weight % of polyester fibers (Tetoron® manufactured by Toray Industries, Inc.) formed of polyethylene terephthalate having fineness of 1.6 dtex and a fiber length of 51 mm. Then, a three-dimensional hydroentangling treatment was performed. The web was placed on a porous support member made of a metal and two stages of nozzles provided with injection holes each having a diameter of 0.10 mm at an interval of 0.6 mm in the width direction of the web were used to sequentially inject water jets at water pressures of 4 MPa and 5 MPa for entangling. The front and the rear of the web were reversed by a conveyor, the web was placed on a polyester plain-woven mesh (OP-76 manufactured by Nippon Filcon Co., Ltd.) support, and the two stages of the nozzles were used to sequentially inject water jets at water pressures of 5 MPa and 6 MPa for three-dimensional entangling. Thereafter, the web was subjected to contact drying at a temperature of 130° C. with a cylinder dryer. A series of these treatments was performed at a speed of 50 m/min. and a spunlace nonwoven fabric (fiber assembly precursor) having a mass per unit area of 68.8 g/m$^2$ was obtained.

Then, one surface of the spunlace nonwoven fabric was fibrillated through a water-bath ultrasonic process with the use of an ultrasonic processor manufactured by Seidensha Electronics Co., Ltd. at power of 1200 W, a frequency of 20 kHz, the number of stages of five, a water temperature of 25° C., and a speed of 1 m/min. on a support formed with a nylon plain-woven mesh (a wire diameter of 160 μm #200) manufactured by Kansai Wire Netting Co., Ltd. Table 1 shows results of evaluation of the obtained fiber assembly.

EXAMPLE 5

A semi-random web was fabricated with CAD with Tencel® (manufactured by Lenzing AG) having fineness of 1.7 dtex and a fiber length of 38 mm. Then, a three-dimensional hydroentangling treatment was performed. The web was placed on a porous support member made of a metal and two stages of nozzles provided with injection holes each having a diameter of 0.10 mm at an interval of 0.6 mm in the width direction of the web were used to sequentially inject water jets at water pressures of 4 MPa and 5 MPa for entangling. The front and the rear of the web were reversed by a conveyor, the web was placed on a polyester plain-woven mesh (OP-76 manufactured by Nippon Filcon Co., Ltd.) support, and the two stages of the nozzles were used to sequentially inject water jets at water pressures of 5 MPa and 6 MPa for three-dimensional entangling. Thereafter, the web was subjected to contact drying at a temperature of 130° C. with a cylinder dryer. A series of these treatments was performed at a speed of 50 m/min. and a spunlace nonwoven fabric (fiber assembly precursor) having a mass per unit area of 70.8 g/m$^2$ was obtained.

Then, one surface of the spunlace nonwoven fabric was fibrillated through a water-bath ultrasonic process with the use of an ultrasonic processor manufactured by Seidensha Electronics Co., Ltd. at power of 1200 W, a frequency of 20 kHz, the number of stages of five, a water temperature of 25° C., and a speed of 0.1 m/min. on a support formed with a nylon plain-woven mesh (a wire diameter of 160 μm #200) manufactured by Kansai Wire Netting Co., Ltd. Table 1 shows results of evaluation of the obtained fiber assembly.

COMPARATIVE EXAMPLE 1

A semi-random web was made with CAD by using viscose rayon (Corona manufactured by OmiKenshi Co., Ltd.) which was regenerated cellulose and had fineness of 1.7 dtex and a fiber length of 40 mm. Then, a three-dimensional hydroentangling treatment was performed. The web was placed on a porous support member made of a metal and two stages of nozzles provided with injection holes each having a diameter of 0.10 mm at an interval of 0.6 mm in the width direction of the web were used to sequentially inject water jets at water pressures of 4 MPa and 5 MPa for entangling. The front and the rear of the web were reversed by a conveyor, the web was placed on a polyester plain-woven mesh (OP-76 manufactured by Nippon Filcon Co., Ltd.) support, and the two stages of the nozzles were used to sequentially inject water jets at water pressures of 5 MPa and 6 MPa for three-dimensional entangling. Thereafter, the web was subjected to contact drying at a temperature of 130° C. with a cylinder dryer. A series of these treatments was performed at a speed of 50 m/min. and a spunlace nonwoven fabric (fiber assembly precursor) having a mass per unit area of 69.0 g/m² was obtained.

Then, one surface of the spunlace nonwoven fabric was fibrillated through a water-bath ultrasonic process with the use of an ultrasonic processor manufactured by Seidensha Electronics Co., Ltd. at power of 1200 W, a frequency of 20 kHz, the number of stages of five, a water temperature of 25° C., and a speed of 1 m/min. on a support formed with a nylon plain-woven mesh (a wire diameter of 160 μm #200) manufactured by Kansai Wire Netting Co., Ltd. Table 1 shows results of evaluation of the obtained fiber assembly.

COMPARATIVE EXAMPLE 2

The same procedure as in Example 1 was performed except that a water-bath ultrasonic process was not performed. The obtained fiber assembly precursor was employed as the fiber assembly as it was (a mass per unit area of 71.1 g/m²) and Table 1 shows results of evaluation.

COMPARATIVE EXAMPLE 3

A semi-random web was made with CAD by mixing 40 weight % of viscose rayon (Corona manufactured by OmiKenshi Co., Ltd.) which was regenerated cellulose and had fineness of 1.7 dtex and a fiber length of 40 mm and 60 weight % of polyester fibers (Tetoron® manufactured by Toray Industries, Inc.) formed of polyethylene terephthalate having fineness of 1.6 dtex and a fiber length of 51 mm. Then, a three-dimensional hydroentangling treatment was performed. The web was placed on a porous support member made of a metal and two stages of nozzles provided with injection holes each having a diameter of 0.10 mm at an interval of 0.6 mm in the width direction of the web were used to sequentially inject water jets at water pressures of 4 MPa and 5 MPa for entangling. The front and the rear of the web were reversed by a conveyor, the web was placed on a polyester plain-woven mesh (OP-76 manufactured by Nippon Filcon Co., Ltd.) support, 10 g/m² of PP-MB (a fiber diameter of 4 μm) was layered on the front surface of the web, and the two stages of the nozzles were used to sequentially inject water jets at water pressures of 5 MPa and 6 MPa for three-dimensional entangling and for making a composite. A spunlace nonwoven fabric (a composite product which was a composite of extremely fine fiber materials) having a mass per unit area of 73.5 g/m² was obtained. Table 1 shows results of evaluation of the obtained fiber assembly.

COMPARATIVE EXAMPLE 4

A plain-woven weave having a mass per unit area of 350 g/m² made of filaments of "Kevlar®" manufactured by Du-Pont Toray Co. Ltd., composed of polyparaphenylene terephthalamide, and having fineness of 1.7 dtex was fibrillated on one surface of the spunlace nonwoven fabric through a water-bath ultrasonic process with the use of an ultrasonic processor manufactured by Seidensha Electronics Co., Ltd. at power of 1200 W, a frequency of 20 kHz, the number of stages of five, a water temperature of 25° C., and a speed of 1 m/min. on a support formed with a nylon plain-woven mesh (a wire diameter of 160 μm #200) manufactured by Kansai Wire Netting Co., Ltd. Table 1 shows results of evaluation of the obtained fiber assembly.

TABLE 1

| | | Example 1 | Example 2 | Example 3 | Example 4 | Example 5 | Comparative Example 1 | Comparative Example 2 | Comparative Example 3 | Comparative Example 4 |
|---|---|---|---|---|---|---|---|---|---|---|
| Mass Per Unit Area | g/m² | 74.6 | 19.9 | 950 | 68.8 | 70.8 | 69.0 | 71.1 | 73.5 | 1140 |
| Thickness | μm | 420 | 122 | 9512 | 488 | 433 | 423 | 415 | 485 | 2600 |
| Density | g/cm² | 0.18 | 0.16 | 0.10 | 0.14 | 0.16 | 0.16 | 0.17 | 0.15 | 0.44 |
| Void Ratio | % | 88.2 | 89.1 | 93.3 | 90.2 | 89.1 | 89.1 | 88.6 | 88.8 | 69.8 |
| Rupture Strength | MD N/5 cm | 229 | 58 | 440 | 194 | 112 | 125 | 228 | 136 | — |
| | CD N/5 cm | 37 | 8 | 244 | 25 | 19 | 21 | 36 | 24 | — |
| Rupture Elongation | MD N/5 cm | 6 | 5 | 77 | 18 | 15 | 28 | 8 | 31 | — |
| | CD N/5 cm | 109 | 88 | 89 | 155 | 111 | 137 | 103 | 144 | — |
| Network Structure with Fibrils | | Yes | Yes | Yes | Yes | Yes | No | No | No | No |
| Ratio of Fibrillation | % | 9.3 | 0.3 | 8.9 | 8.8 | 66.3 | 0 | 0 | 0 | 0.5 |
| Fibrils Extending in Direction of Thickness | Count | 144 | 22 | 105 | 53 | 433 | 0 | 0 | 0 | 0 |

TABLE 1-continued

|  |  | Example 1 | Example 2 | Example 3 | Example 4 | Example 5 | Comparative Example 1 | Comparative Example 2 | Comparative Example 3 | Comparative Example 4 |
|---|---|---|---|---|---|---|---|---|---|---|
| Water Retention Ratio | % | 610 | 685 | 1210 | 820 | 551 | 753 | 796 | 803 | 173 |
| Diffusibility | MD mm | 47 | 44 | 58 | 39 | 48 | 21 | 22 | 7 | 6 |
|  | CD mm | 29 | 26 | 48 | 27 | 32 | 14 | 14 | 4 | 5 |
|  | MD × CD | 1363 | 1144 | 2784 | 1053 | 1536 | 294 | 308 | 28 | 30 |
| Adhesiveness | N | 1.68 | 1.25 | 1.75 | 1.32 | 1.58 | 0.82 | 0.81 | 1.55 | 0.35 |
| Release Ratio | % | 59 | 63 | 58 | 63 | 62 | 35 | 39 | 58 | 14 |
| Surface Frictional Strength | Peel-Off of Surface | No | No | No | No | No | No | No | Yes | No |

It should be understood that the embodiments and the examples disclosed herein are illustrative and non-restrictive in every respect. The scope of the present invention is defined by the terms of the claims, rather than the description above, and is intended to include any modifications within the scope and meaning equivalent to the terms of the claims.

INDUSTRIAL APPLICABILITY

As the fiber assembly according to the present invention in a form of a sheet is employed as a liquid absorbent sheet-like article, it can serve as an ink absorber, an incontinence pad, a surface material for a sanitary pad, and a surface material for a paper diaper, and it can be adopted for articles used for a purpose to absorb a liquid such as a face mask, an application sheet, a wet wiper, an antiperspirant sheet, a wet wipe, and a liquid filter or articles used with a liquid being absorbed therein or a composite member achieving a desired function by using high diffusibility of the fiber assembly according to the present invention, without being limited.

When the fiber assembly according to the present invention has a high ratio of fibrillation at opposing ends in the direction of thickness, a surface to be used is not particularly limited. With one side in the direction of thickness of the fiber assembly being defined as a front surface side and the other side in the direction of thickness being defined as a rear surface side, the fiber assembly can suitably be applied to such an application that a liquid is hardly diffused over a front surface and the liquid is diffused over a rear surface with a network structure (such as an incontinence pad surface material, a surface material for a paper diaper, a surface material for a sanitary pad, and an agricultural water retention sheet).

When the fiber assembly according to the present invention has a fibrillated central portion in the direction of thickness and only any end portion thereof in the direction of thickness is high in ratio of fibrillation, the fiber assembly can suitably be applied to such an applications as a filter, for example, by using a gradient of a fibril structure. When the central portion in the direction of thickness is fibrillated and opposing end portions in the direction of thickness are high in ratio of fibrillation, the fiber assembly can suitably be applied to such an application as a cleansing sheet which is, for example, less irritating to the skin and has high cleansing capability.

REFERENCE SIGNS LIST 1, 1', 1" fiber assembly; 2 fiber; 3 fibril; 3a fibril extending in direction of thickness of fiber assembly; 4 network structure; 5 other fiber; Z direction of thickness of fiber assembly; F virtual straight line representing direction of extension of fibril; 11 branch portion; 12 trunk portion; 13 branch portion; 14 trunk portion; 15 branch portion; 16 branch portion; 17 trunk portion; 20 sample; 20a grip portion; 21 table; 22 clip; 23 pulley; 24 polyamide thread; 25 load cell.

The invention claimed is:

1. A fiber assembly, comprising:
    a fibril which is a part of a fiber extending in a direction of thickness of the fiber assembly; and
    a network structure formed with a binding portion resulting at least from binding between fibrils and binding between a fibril and a fiber in at least any end portion in the direction of thickness of the fiber assembly,
    wherein a region where an average number of fibrils extending in the direction of thickness of the fiber assembly is not smaller than 10 when 100 sections of 300 μm wide×a thickness of the fiber assembly in a cross-section in a direction perpendicular to a direction of a length of fiber are observed.

2. The fiber assembly according to claim 1, wherein a void ratio of the fiber assembly is not lower than 50%.

3. The fiber assembly according to claim 1, having a rupture strength not lower than 3 N/5 cm and a rupture elongation not higher than 300%.

4. The fiber assembly according to claim 1, which is in a form of a sheet.

5. The fiber assembly according to claim 4, which is a nonwoven fabric.

6. The fiber assembly according to claim 5, having a mass per unit area from 10 to 1000 g/m$^2$.

7. The fiber assembly according to claim 5, having a thickness from 0.05 to 10 mm.

8. The fiber assembly according to claim 5, having an apparent density from 0.01 to 0.5 g/cm$^3$.

9. The fiber assembly according to claim 5, which is a spunlace nonwoven fabric.

10. The fiber assembly according to claim 1, formed from a trunk portion that retains a form of a sheet and a branch portion having the network structure,
    wherein a ratio of a diameter of fibers forming the trunk portion to a diameter of fibers forming the branch portion is from 5000:1 to 5:1.

11. The fiber assembly according to claim 1, having a ratio of fibrillation within a range from 0.1 to 70%,
    wherein the ratio of fibrillation is calculated from an expression ratio of fibrillation (%)=$(A-B)/A\times 100$ where A represents an average value of a cross-sectional area of 100 fibers in a direction perpendicular to a direction of length of fiber in a region formed with fibers without fibrils of the fiber assembly on an outer side and B represents an average value of a cross-sectional area of 100 fibers in a region including fibers with fibrils on an outer side formed in at least any end portion in the direction of thickness of the fiber assembly.

12. The fiber assembly according to claim 1, wherein fibers with fibrils are cellulose fibers manufactured through solvent spinning.

13. The fiber assembly according to claim 1, wherein the network structure is formed by binding between a fibril and a fiber main body, binding between fibrils, and entangling between fibrils.

14. The fiber assembly according to claim 1, wherein a value for (a diffusion length in the machine direction of the fiber assembly)×(a diffusion length in the cross direction of the fiber assembly) is not smaller than 400.

15. A liquid absorbent sheet-like article, comprising the fiber assembly according to claim 5.

16. A method of manufacturing the fiber assembly according to claim 1, the method comprising:
  forming a fiber assembly precursor by assembling a plurality of fibers; and
  forming a network structure having a binding portion resulting at least from binding between fibrils and binding between a fibril and a fiber by forming fibrils extending in a direction of thickness of the fiber assembly by applying cavitation energy from at least one side in a direction of thickness of the fiber assembly precursor.

* * * * *